United States Patent [19]
Oishi et al.

[11] 4,131,490
[45] Dec. 26, 1978

[54] METHOD FOR SCARFING SURFACE DEFECTS OF A METAL PIECE

[75] Inventors: Akiyoshi Oishi; Tamotsu Harada; Takashi Ishikawa, all of Kitakyushu, Japan

[73] Assignee: Nippon Steel Corporation, Tokyo, Japan

[21] Appl. No.: 590,806

[22] Filed: Jun. 27, 1975

[30] Foreign Application Priority Data

Jul. 1, 1974 [JP] Japan .................................. 49-74322

[51] Int. Cl.² .............................................. B23K 7/06
[52] U.S. Cl. ...................................... 148/9.5; 266/51; 364/472; 364/507; 358/10
[58] Field of Search ...................... 148/9.5, 9.6, 9; 266/51; 83/8, 71, 371, 522; 178/DIG. 34, DIG. 37; 340/146.3 B; 235/151.11, 151.3; 209/111.6; 324/37

[56] References Cited

U.S. PATENT DOCUMENTS

| 2,950,049 | 8/1960 | Mazer et al. | 340/146.3 B |
| 3,196,393 | 7/1965 | Siegemund | 340/146.3 B |
| 3,245,842 | 4/1966 | Miller et al. | 148/9.5 |
| 3,513,320 | 5/1970 | Weldon | 209/111.6 |
| 3,633,010 | 1/1972 | Svetlichny | 148/9.5 |
| 3,676,959 | 7/1972 | Forster | 324/37 |
| 3,822,632 | 7/1974 | Chigiotti | 90/13 R |

Primary Examiner—W. Stallard

[57] ABSTRACT

There is described a marking method for distinguishing the kind, depth, position and area of surface defects of a metal piece as well as a method for detecting marks on the metal piece and a method for arranging detected signals in a electronic computer to automatically control scarfing. Shapes and colors of the marks respectively correspond to either the kind or depth of the surface defects of the metal piece. The marks are detected by a photosensitive means which can recognize colors of the marks, for example, industrial color television camera. Output signals of the camera are transmitted to the electronic computer. The computer arranges the signals and processes them to automatically control the scarfing machine.

9 Claims, 21 Drawing Figures

METHOD FOR SCARFING SURFACE DEFECTS OF A METAL PIECE

BACKGROUND OF THE INVENTION

The invention relates to the automation of scarfing surface defects of a metal piece such as steel slab, for example.

In the prior art practice the scarfing or cutting of a metal piece such as steel slab to remove surface defects has been accomplished by sensing the position, extent, type and depth of surface defects through manual intervention and manually operating a scarfing nozzle or cutting machine. For removal of surface defects of the metal piece, it is impossible to determine the scarfing procedure within a sufficiently short time interval which would allow the defects dispersed along the slab surface to be scarfed within the minimum period of time. As a result, the machine capability is constrained by the human ability. Where the scarfing machine includes a plurality of nozzles, a manual operation of issuing simultaneous scarfing instructions to the plurality of nozzles becomes even more difficult, the more the number of nozzles, thereby precluding an efficient scarfing treatment.

Another factor which stands in the way of the automation of the control of the scarfing machine has been the lack of an effective recognition system which deals with information representing the surface defects of the metal piece.

Hand scarfing is unfavorable from the standpoint of the health administration of operators, and is also limited in the processing capability.

In view of the difficulties mentioned above in connection with the conventional method of treating surface defects of a metal piece, it is an object of the invention to provide a process of treating surface defects of a metal piece which can be automated to a high level.

The Japanese patent specification No. 277,271 describes a method and apparatus for automated scarfing of surface defects of a metal piece. In the method, single color marks are spread on defects of a metal surface by workers, or luminous substance is impregnated in the defects of a metal surface automatically. Photo-sensitive means detects the marks or luminous substance. Detected signals of the photo-sensitive means are recorded on electro-magnetic tape or tapes. The tapes travels in synchronism with the movement of the metal piece. The recorded signals on the tapes are then read out at the scarfing position to scarf the defects on which the marks or luminous substance are spread or impregnated. A time adjustment means to determine the scarfing position includes the tapes and driving mechanism for the tapes. The time adjusting means determines the time interval between the detection of the defects by the photo-sensitive means and triggering of scarfing. Thus, the defects detected by the photo-sensitive means are deleted out by scarfers at the lower reaches of the metal transmitting path. However, the metal piece travels continuously, so that defects at the head end position of the metal piece can not be deleted out thoroughly, because heating of the metal surface by scarfers is not sufficient at the top (head) edge of the metal piece when the metal piece is moving.

Therefore it is preferable to scarf out thoroughly the defects near the top edge of the metal piece.

In another point of view, scarfers have delay times to scarfing out the defects sufficiently, so that when defects exist hear and there, defects which reach the scarfing position within a delay time from a preceeding defect can not be scarfed out thoroughly. In addition, marks spread on the metal surface or luminous substance impregnated in the defects are not uniform, and have breaks, so that scarfings may stop in intermediate positions of the defects. Therefore, stable and uniform scarfing upon a continuous defect is frequently not achieved.

Further, the metal piece may sway in transverse direction, so that modification of the scarfer's position in the transverse direction may be required.

SUMMARY OF THE INVENTION

The object of the present invention is to provide a method for scarfing surface defects of a metal workpiece, wherein sufficient scarfing throughout the defects can be practiced automatically.

In accordance with the invention, a method of treating the surface defects of a metal piece comprises the steps of marking surface defects of a metal piece with a pattern which includes combinations of figures and colors representing the position, extent, type and depth of the surface defects, sensing the pattern with a mark detector, inputting the detected pattern to an electronic computer to cause it to form a metal surface image in a mesh configuration, thus allowing the computer to recognize the position, extent, type and depth of the surface defects on the bases of the inputs. The computer, on the basis of the recognition of the surface defects, then corrects the areas of the metal surface to be scarfed by a scarfing nozzle and calculates an optimum depth to be scarfed for each of the areas to be scarfed as well, as calculates the minimum time of the scarfing procedure. The corrected and calculated information from the computer is then sent to a scarfing machine or any other ancillary equipment, thereby allowing automatic scarfing of the surface defects.

The surface defect of a metal piece must be identified separately in terms of the position, extent, type and depth of the respective defect. At the present status of technology, the best accuracy which can be expected is that achieved by visual inspection. For this reason, in accordance with the invention, the surface defects of a metal piece are visually inspected by an operator, who marks the respective surface defects with patterns or combinations of figures and colors which are accorded to the position, extent, type and depth of the surface defects, respectively. An industrial color television camera is employed as a mark detector to supply a corresponding information into the memory of an electronic computer to form a metal surface image in a mesh configuration. By way of example, the major surface as well as the edge face of the metal piece is covered by a grid of meshes measuring 30 millimeters by 25 millimeters so as to permit an addressing of the memory of the computer to enable a storage, in response to the inputs from the mark detector, of patterns indicating the position, extent and type of the defects. In this manner, the computer is capable of recognizing and storing information relating to the surface defects of the metal piece by distinguishing the patterns associated with the respective metal pieces by pattern recognition.

On the basis of the information relating to the surface defects of the metal piece which is recognized by and stored in the computer, the latter calculates an optimum scarfing depth for each defect area, corrects areas to be scarfed by a scarfing nozzle assembly for each scarfing to operation unit, and ultimately establishes an optimum scarfing depth for each area unit of areas to be scarfed.

By way of example, if the flame produced by a single nozzle has a width of 200 mm and the metal piece or the single nozzle is moved in increments of 90 mm, a single scarfing operation unit for the single nozzle is defined by an area of 200 × 90 mm. If a flaw which measures 200 mm wide and 1800 mm long is recognized, this represents one area to be scarfed, which is broken into 20 operation units when the single nozzle is used alone. An optimum scarfing depth of 10 mm, for example, is established for this area to be scarfed.

When using a scarfing machine which has a single scarfing nozzle, the computer calculates and establishes a minimum time scarfing procedure in order to minimize the period of time required for the scarfing operation.

Additionally, the computer is externally supplied with information which represents the relative position and the relative speed between the scarfing machine and the metal piece to be scarfed and converts them into electrical signals which are required to control the operation of the scarfing machine and the metal piece conveyor based on the optimum scarfing depth established for each operation unit, the minimum time scarfing procedure of the scarfing nozzle, and the relative speed of the metal piece and the scarfing machine. The electrical signals control and drive the scarfing machine and roller table drive motor, for example.

Further details of the invention will be described more fully below with reference to the drawings.

DESCRIPTION OF PREFERRED EMBODIMENTS

Figure 1:
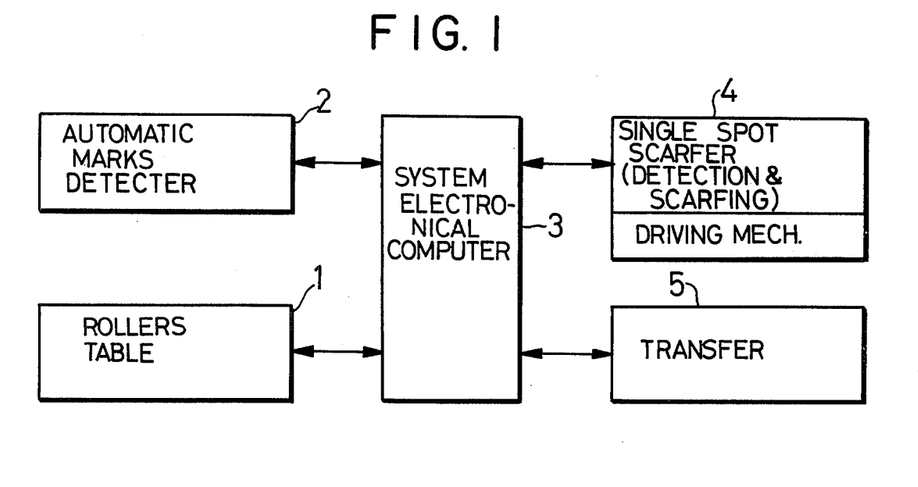
FIGS. 1 to 8 are schematic views illustrating the method of treating surface defects of a metal piece in accordance with the present change.

Referring to FIG. 1, a metal piece which is manually marked with patterns is conveyed on a roller table 1 while being scanned by a mark detector 2, for example, an industrial color television camera which is fixed on the table. The scanning takes place by utilizing particular scanning lines of the industrial television camera so as to subdivide the entire surface of the metal piece into a mesh configuration, thereby detecting the presence or absence of a mark in each mesh area. The presence of a mark also produces an input of a corresponding color information. In this manner, information relating to surface defects of the metal piece is detected in accordance with the patterns on the surface thereof without contact therewith and provides inputs to an electronic computer 3. Such detection takes place for the upper and lower major surfaces as well as the both lateral surfaces of the metal piece. Also, the detection obtains information relating to the relative position of the metal piece and the respective patterns is also introduced into the computer 3. A metal surface image in a mesh configuration is formed within the computer 3 in accordance with the input pattern signals, thus achieving a recognition of the position and extent of surface defects of the metal piece. Also the type and depth of the surface defects are recognized, all of which are utilized to calculate an optimum scarfing depth for the extent of surface defects. The marking method, shapes of the marks and colors of the marks are described by the following examples.

EXAMPLE 1

Defect information include kind, depth, position and area of the defects.

(1) The kinds of the defects are described by the shapes of the marks.

(2) The areas are indicated by the extensions of the marks. An example is indicated in the table 1.

Table 1

| Kinds of the defects | Shapes of the marks | Areas of the defects (extensions of the marks) | Remarks |
|---|---|---|---|
| Cracks | □ | within the line | including lozenges and regular squares |
| Scabs | ○ | within the line | including ellipses |
| Non-metalic inclusions | × | areas of line extension | |
| Others | △ | within the line | |

(3) the positions of the defects are indicated by the positions of the marks.

(4) Depths of the defects are indicated by colors of the marks, for example, the depth is indicated as described in the table 2.

Table 2

| Depthes of the defects | Colors of the marks |
|---|---|
| 0 ~ 3 mm | red |
| 4 ~ 6 mm | blue |
| 7 ~ 9 mm | yellow |
| 10 ~ 12 mm | white |

EXAMPLE 2

Defect information include kind, depth, position and area of the defects.

(1) The kinds of defects are indicated by colors of marks as shown in table 3.

Table 3

| Kinds of the defects | Colors of the marks |
|---|---|
| cracks | red |
| scabs | blue |
| non-metalic inclusions | yellow |
| others | white |

(2) The areas are indicated by the extension of the marks.

(3) The positions of the defects are indicated by the positions of the marks.

(4) The depth of the defects are indicated by the shape of the marks, in which the marks represent depth of the defects as numerals.

Figure 10:
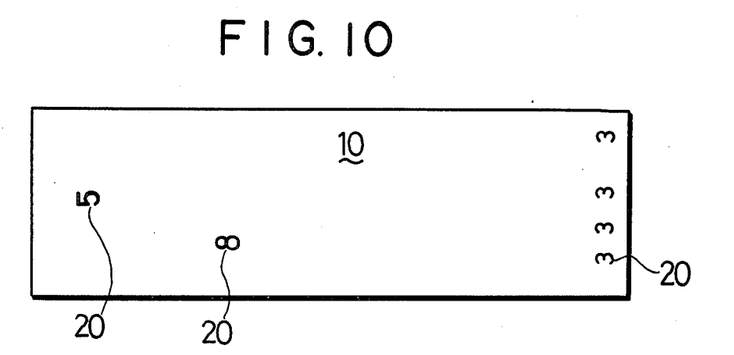
FIG. 10 is a schematic view illustrating the surface of a metal plate on which marks are written.

FIG. 10 shows marks pattern on a metal surface, whereby the marks are painted in accordance with the example 2. In the FIG. 10, 10 denotes a slab and 20 denotes marks.

In another example, the depth of the defects is assumed to correspond to the kinds of the defects, in which case information of the kind of mark also indicate depth of the defect. Alternatively, information of the kind of mark may be deleted.

The marks on a metal surface are detected by photosensitive means, preferrably an industrial color television camera, and the detected signals of the camera are transmitted to an electronic computer.

Figure 11:
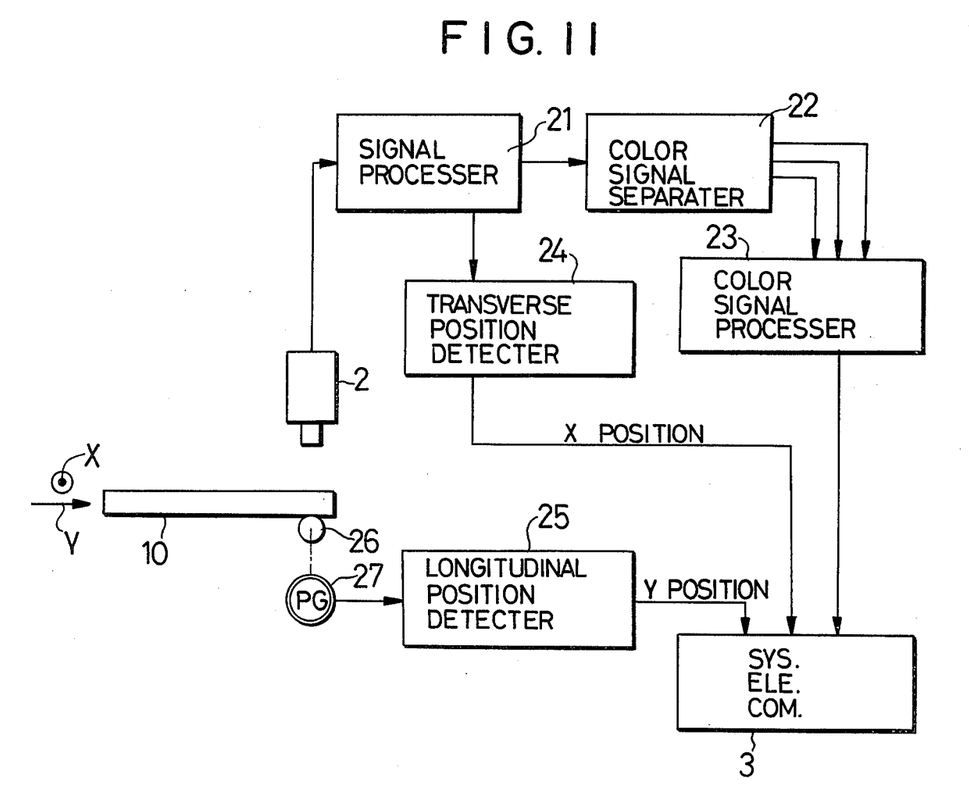
FIG. 11 is a schematic view illustrating the detection and signal processing system for carrying out the present invention.

FIG. 11 shows diagramatically a detection system for the marks. In which case, sweep lines of the color television camera are parallel to the longitudinal direction Y and perpendicular to the transverse direction X. A mesuring roll 26 rotates in correspondence with the movement of the slab or a metal plate 10. A pulse generator 27 generates pulses in correspondence with the rotation of the mesuring roll 26. The pulses are counted by a longitudinal position detector 25. Thus signals which represent detected Y position are transmitted to the computer 3 by the detector 25. Output signals of the color television camera 2 are transmitted to a signal processor 21, in which X positions of sweep lines are converted to X position signals and transmitted to a X position detector 24. The detector 24 transmits signals representing X positions to the computer 3. Signals representing the detected marks from the camera 2 are transmitted to a color signal separator 22 through the signal processor 21. The separator 22 separates out color signals, for example red signal, green signal and blue signal, and transmits them to a signal processor 23. The signal processer converts the color intensity analog signals to digital signals, and transmits them to the computer 3.

Figure 12:
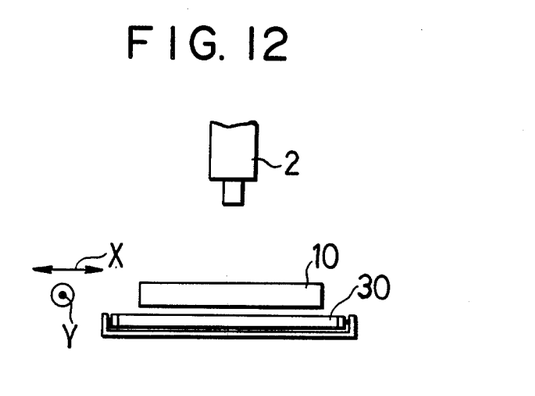
FIG. 12 is a schematic view illustrating a light source for clarifying edges of a metal plate.
Figure 13A:
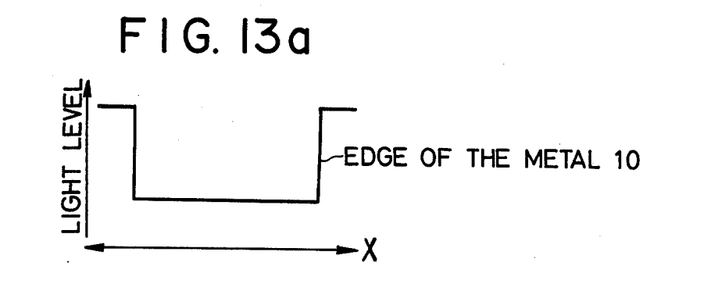
FIGS. 13a to 13b are schematic views illustrating light levels detected by a color television camera.
Figure 13B:
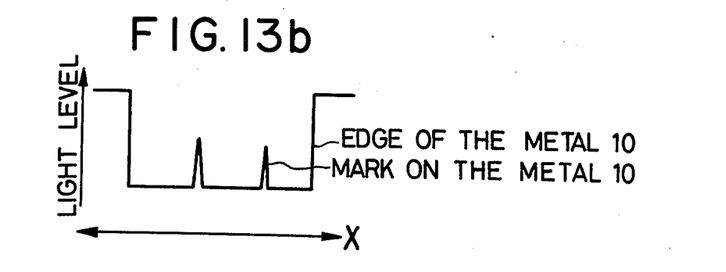
Figure 13C:
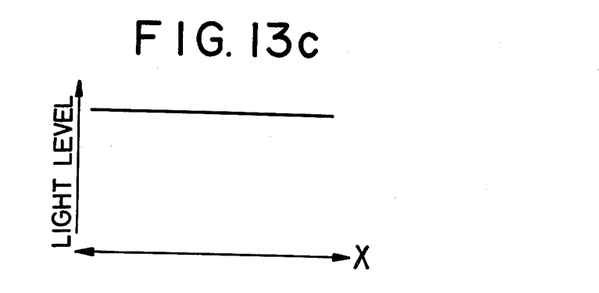

Color indication can be done by using the known I - Q method. For example, color intensity of red, green and blue of digital value are denoted by R, G and B respectively and the following formula are used, $$I = 0.60 \cdot R - 0.28 \cdot G - 0.32 \cdot B$$

$$Q = 0.21 \cdot R - 0.52 \cdot G + 0.31 \cdot B$$

values of $\theta = \tan^{-1} Q/I$ represent colors, for example pink, lemon yellow, emerald green, cobalt blue and etc. Thus digital value $\theta$ which represents colors, can be calculated in the computer 3 or in the signal processor 23. As shown in FIG. 12, light source 30 of longitudinal shape preferably exists at the back side of the metal piece 10. In this case light levels detected by the camera 2 are distributed as shown in FIG. 13a and 13b, whereby the FIG. 13a shows no marks and the FIG. 13b shows marks. The side edges of the metal 10 can be recognized clearly. When the metal 10 is not advanced to the position under the camera 2, the detected light level is shown as in FIG. 13c. Therefore, when the detected light level changes from FIG. 13c to FIG. 13a or 13b it means the detection of the top edge of the metal plate 10. Thus detection of the top edge of the metal plate 10 can be recognized in the processor 21 or 23. As seen in the FIG. 13a and 13b, marks on and edges of the metal plate 10 can be recognized from the output signal of the camera 2, and transmitted to the processor 21 or 23. Therefore, signals which represent top and tail edges as well as side edges of the metal plate 10, mark positions (X, Y), and colors of the marks are obtained and transmitted to the computer 3.

Figure 14:
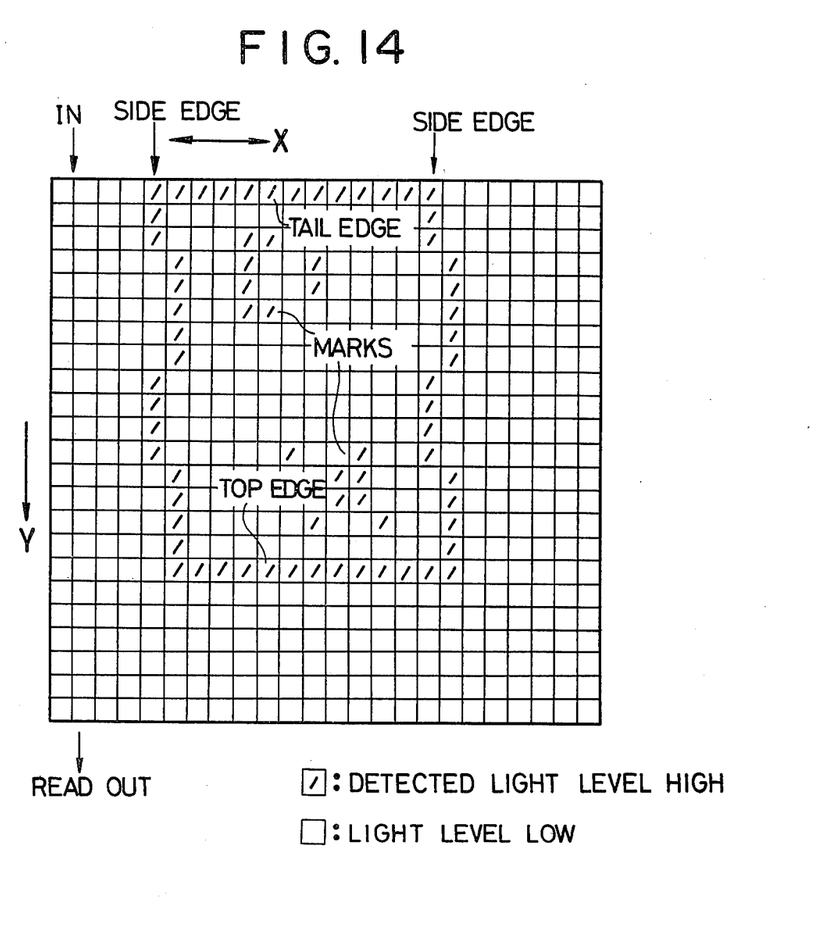
FIGS. 14 to 18 are schematic views illustrating a memory pattern memorized in a electronic computer.
Figure 15:
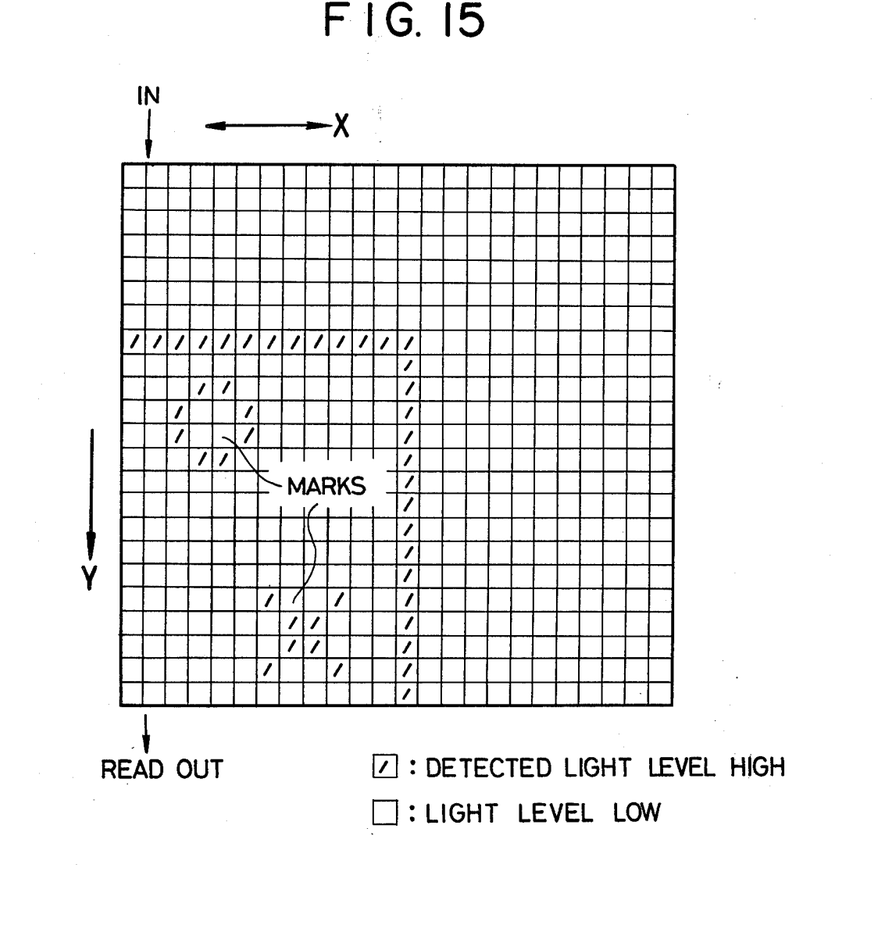

The computer 3 memorizes the signals, and forms a memory pattern which corresponds to the metal plate surface condition. The memory pattern in the computer 3 can be indicated diagramatically as shown in FIG. 14, the outermost high level [1] indicates edges of the metal plate 10. The displacement of the outer high level positions means transverse movement of the metal plate. The memory pattern is modified and shifted in the computer 3 as shown in FIG. 15, to eliminate the error caused by the transverse movement of the metal plate 10.

Figure 16:
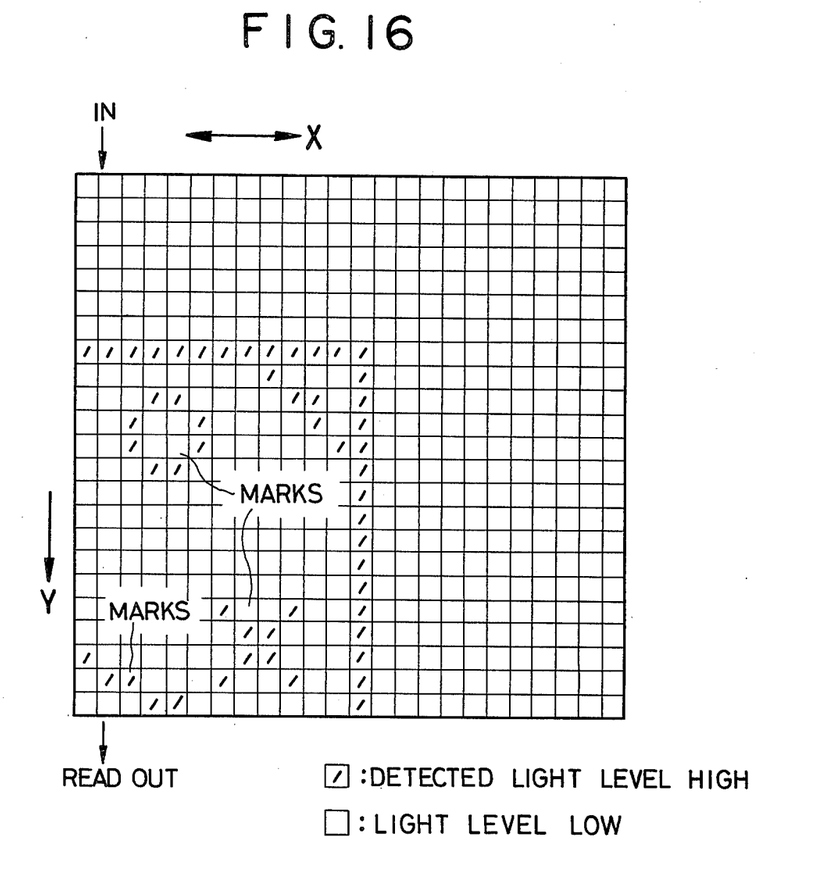

As shown in FIG. 16, when there are marks (defects) at the top edge position, the scarfing should be started from the top edge, and the metal plate 10 should be stopped at the starting of the scarfing, otherwise scarfing will fail near the top edge. According to the present invention, the computer detects the marks (in memory) which intersect with the edges. Recognition of these and other marks can be done with known pattern recognition procedures in the computer 3. The marks which intersect the top edge or side edges near the top edge means defects at top edge area. Thus the computer generates stop these signals and transmits out it to the metal or nozzle transport control means to stop the metal or scarfing nozzle at a predetermined position at which the top edge of the metal plate is under the scarfing nozzles, or nozzle.

Figure 17:
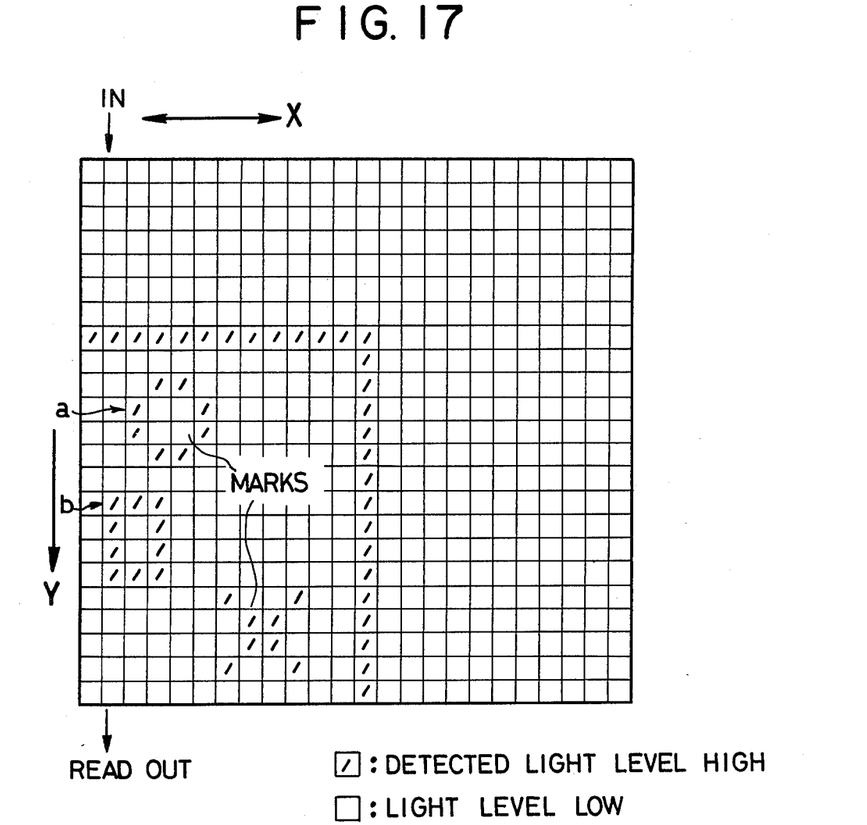

As shown in FIG. 17, the distance or time interval between mark a and b is quite short as compared with the delay time of scarfers. The computer compares distance between the marks and generates continuation signals when the distance (time interval) between the marks is shorter than the delay time (distance) of the scarfers.

Figure 18:
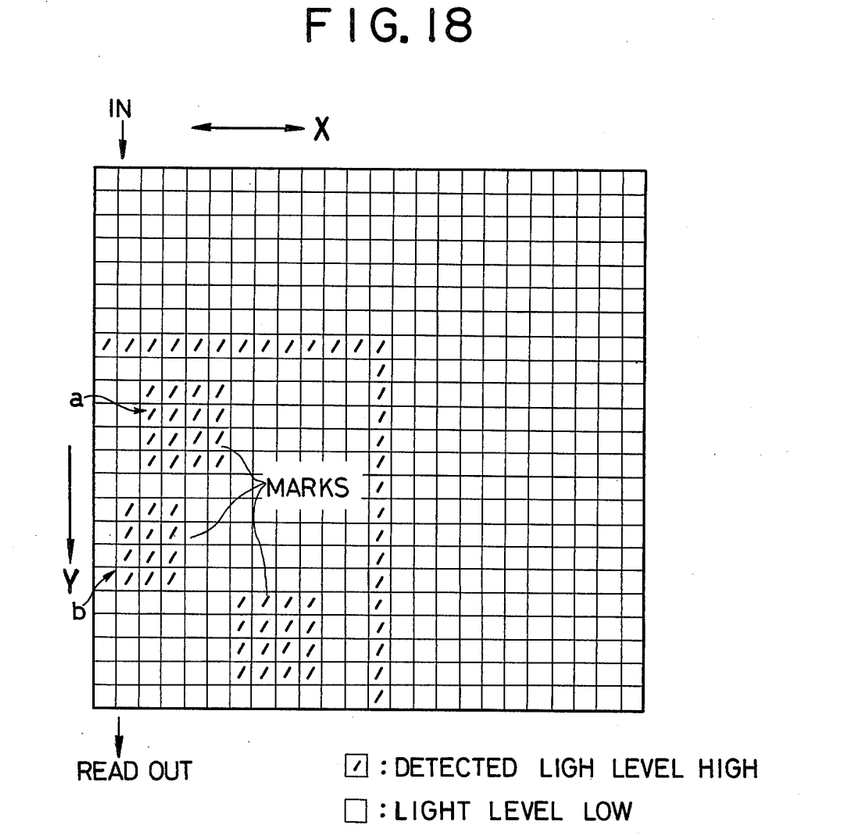

Finally or in an appropriate stage of processing the memorized pattern, areas of marks, namely, areas to be scarfed is determined as shown in FIG. 18, the areas cover all the extension of the marks.

The extent of surface defects recognized in the metal surface image is edited into scarfing areas in terms of the unit areas of scarfing achieved by a scarfing nozzle, in the computer 3. Simultaneously an optimum scarfing depth is calculated for each scarfing area. Where the scarfing machine is a single nozzle machine, the nozzle is designed to have a freedom of movement in two dimensions and the nozzle head is enabled to rotate for the convenience of calculating a minimum time scarfing procedure for the nozzle. The optimum scarfing depth for each scarfing area which is edited in terms of unit areas of scarfing by the nozzle as well as the minimum time scarfing procedure of the scarfing nozzle are input into the scarfing machine. The input information is effective to move the scarfing machine 4 through a transfer unit 5, thus sequentially scarfing the metal piece which remains at rest to a scarfing depth which is established for each edition area.

Figure 2:
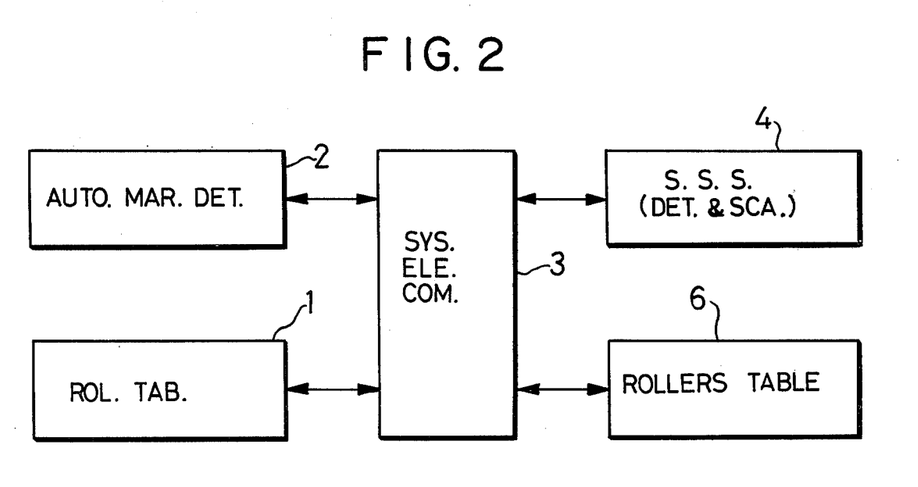

Alternatively, the scarfing machine 4 may remain at rest, and the metal piece may be carried on a roller table 6 during the time it is scarfed to a given depth, as shown in FIG. 2.

Figure 3:
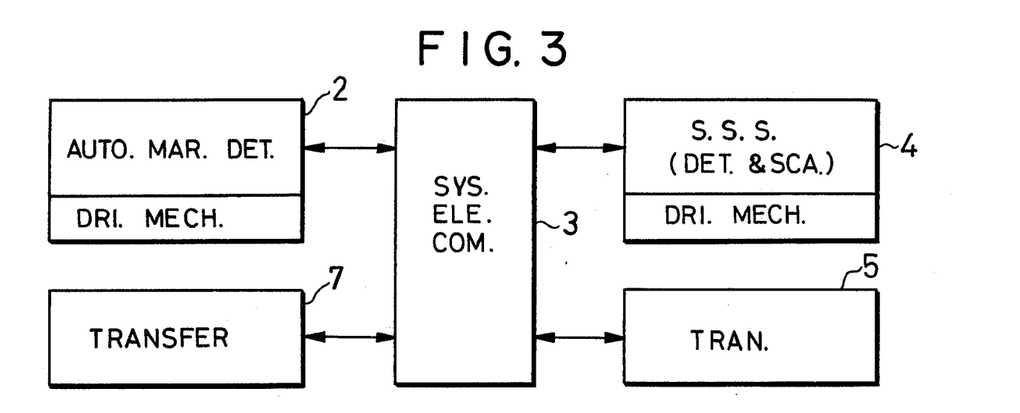

While in the arrangements of FIGS. 1 and 2, the automatic mark detector 2 remains at rest while the metal piece is carried on the roller table 1, FIG. 3 shows that the metal piece remains at rest while the automatic mark detector 2 is carried by a transfer unit 7 so as to detect patterns associated with the surface defects of the metal piece in a sequential manner. In other respects, the arrangement is similar to that shown in FIG. 1.

Figure 4:
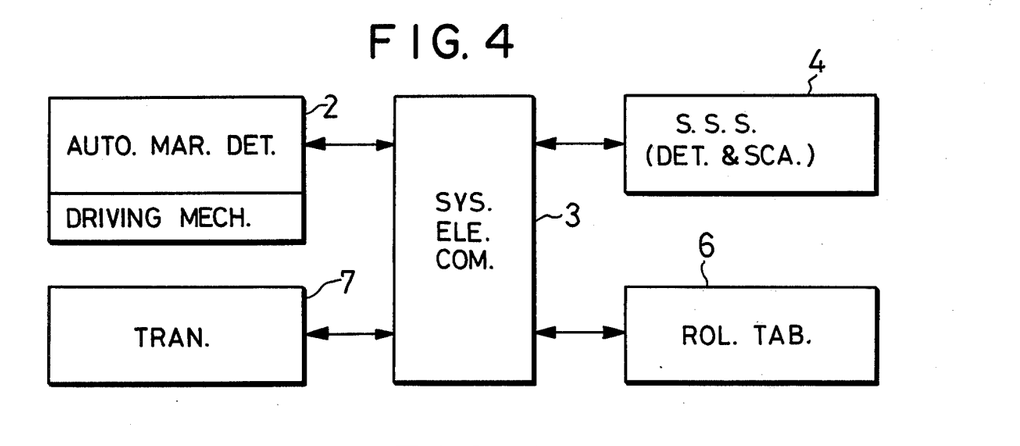
Figure 5:
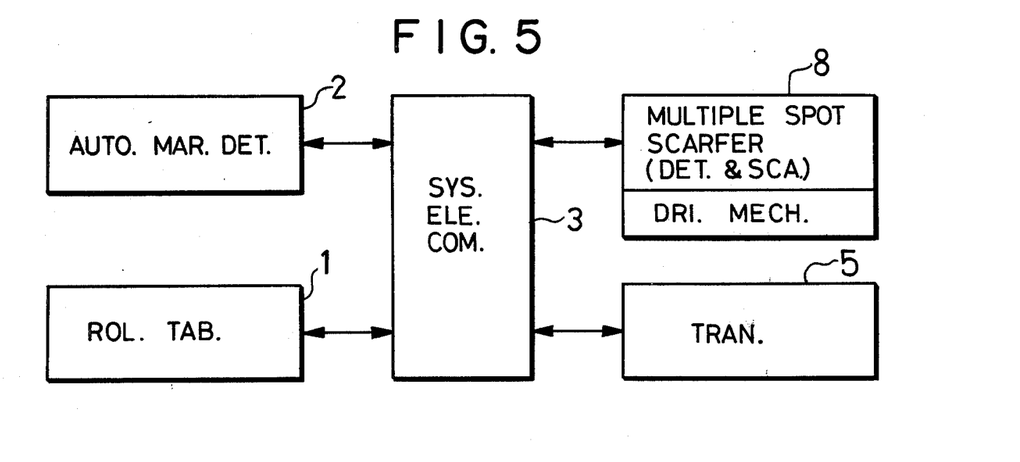
Figure 6:
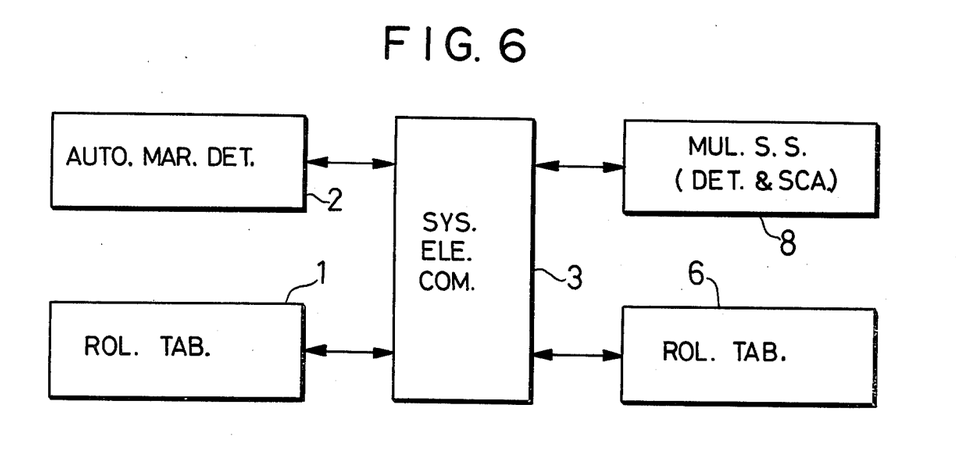
Figure 7:
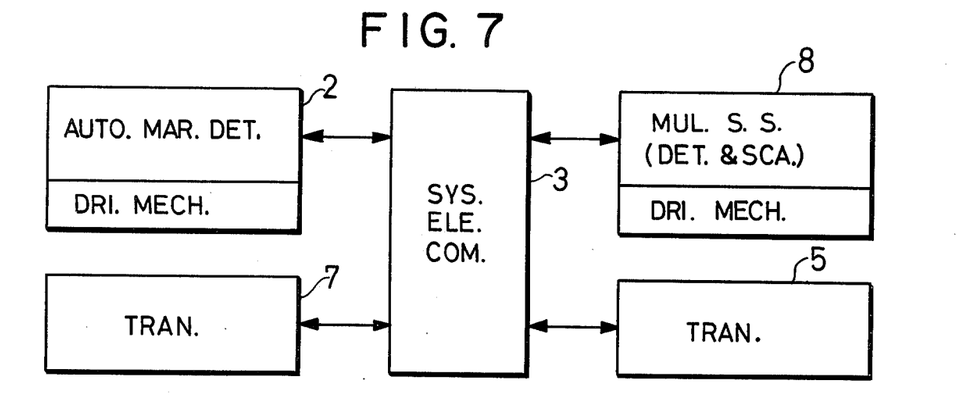
Figure 8:
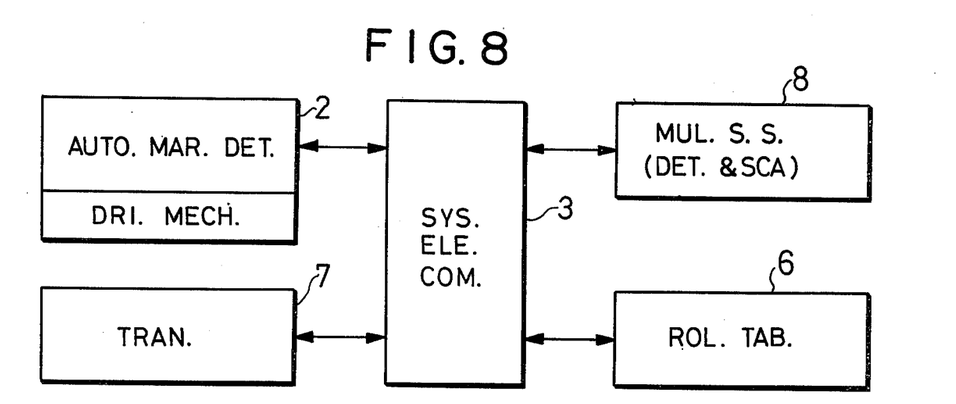

FIG. 4 shows a system which represents a compromise between those shown in FIGS. 2 and 3.

FIGS. 5, 6, 7 and 8 show arrangements constructed generally in the similar manner as the corresponding systems illustrated in FIGS. 1 to 4, respectively but in which a scarfing machine 8 having a plurality of nozzles which are equal in number to the number of scarfing areas and which are disposed crosswise of the metal piece. In any of these arrangements shown in FIGS. 5 to 8, it is not necessary to produce a two dimensional displacement of the scarfing nozzles, which are only moved along the length of the metal piece.

Figure 9A:
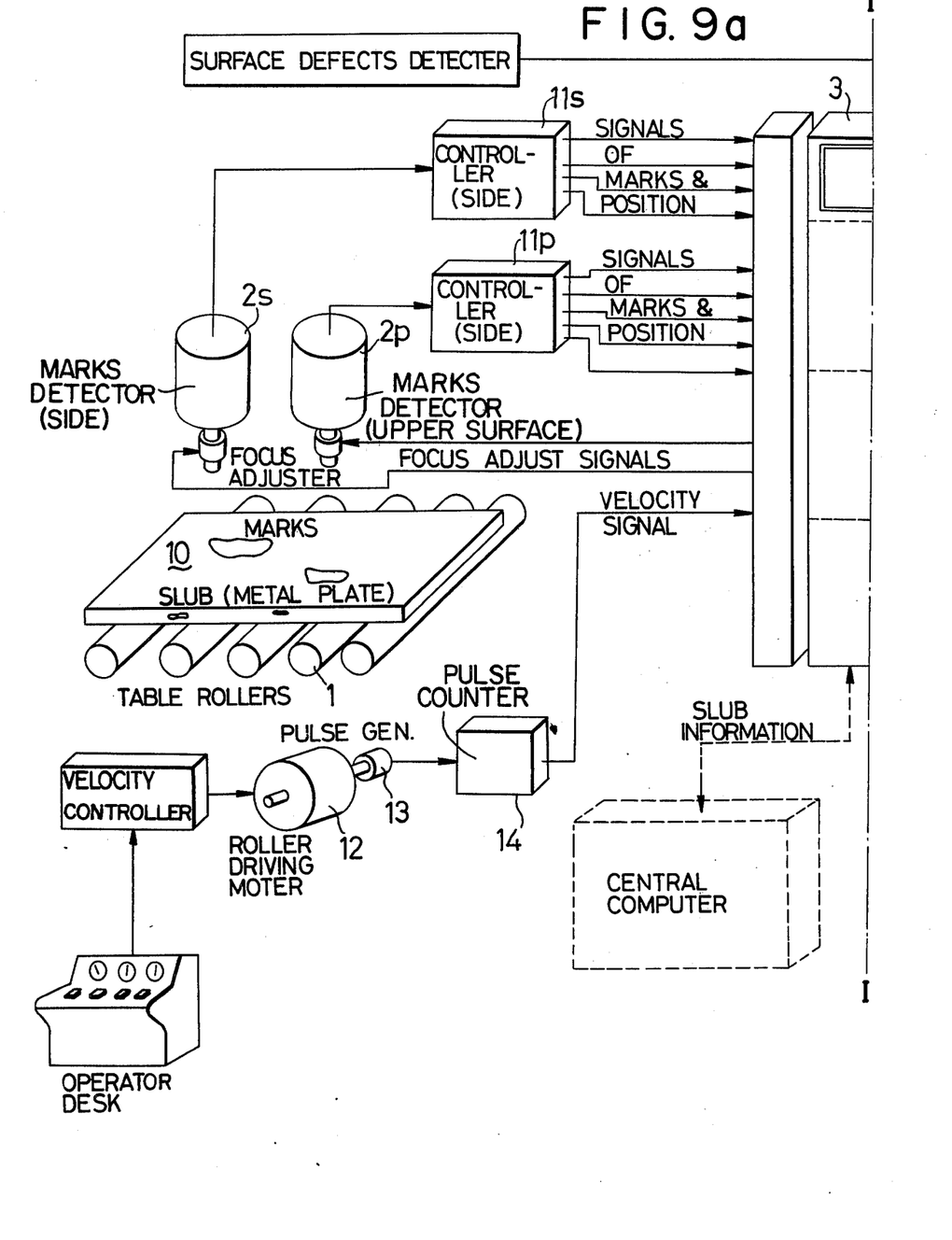
FIGS. 9a, 9b and 9c are block diagrams of one embodiment of an apparatus which is used to carry out the method according to the invention.
Figure 9B:
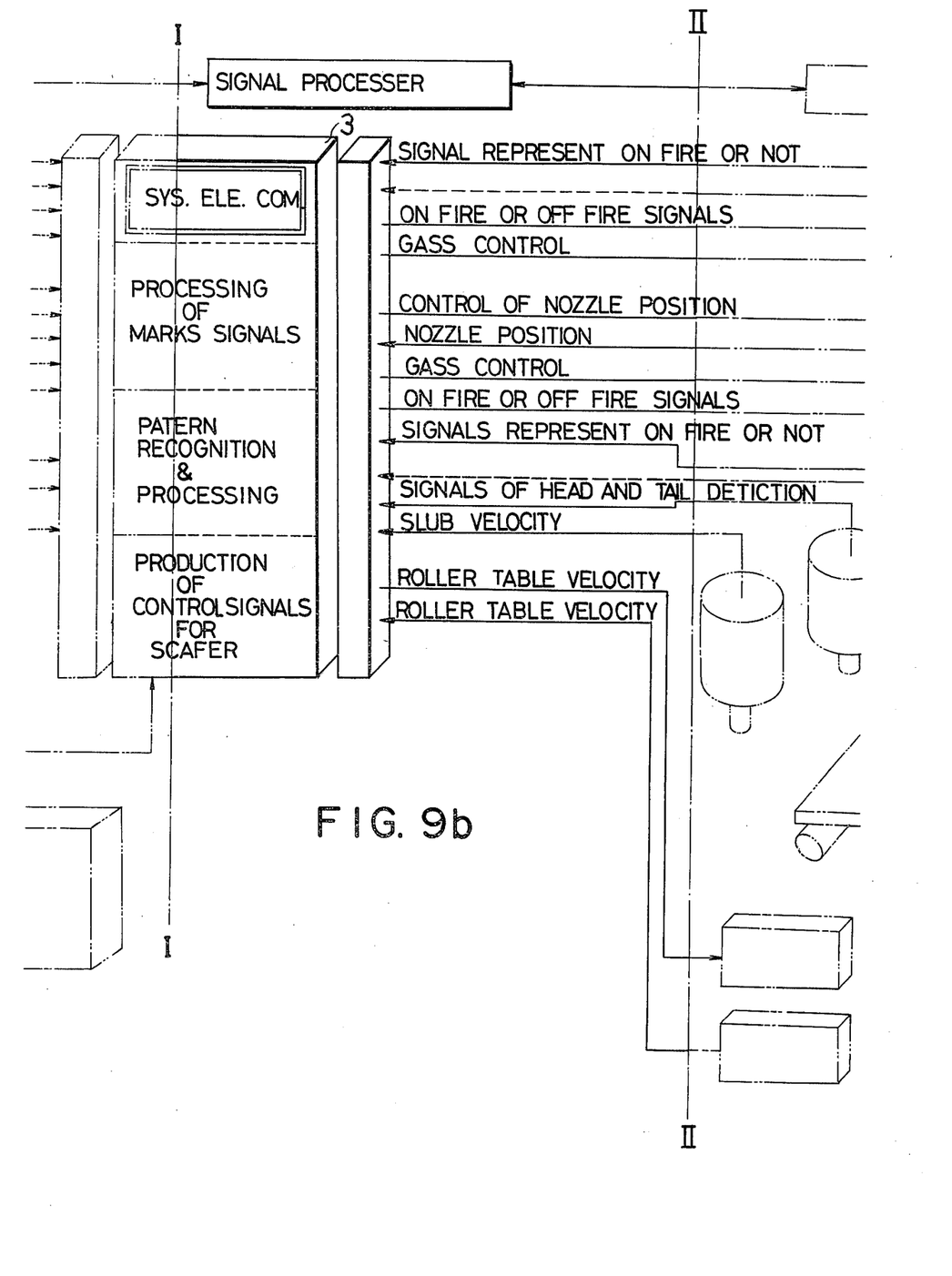
Figure 9C:
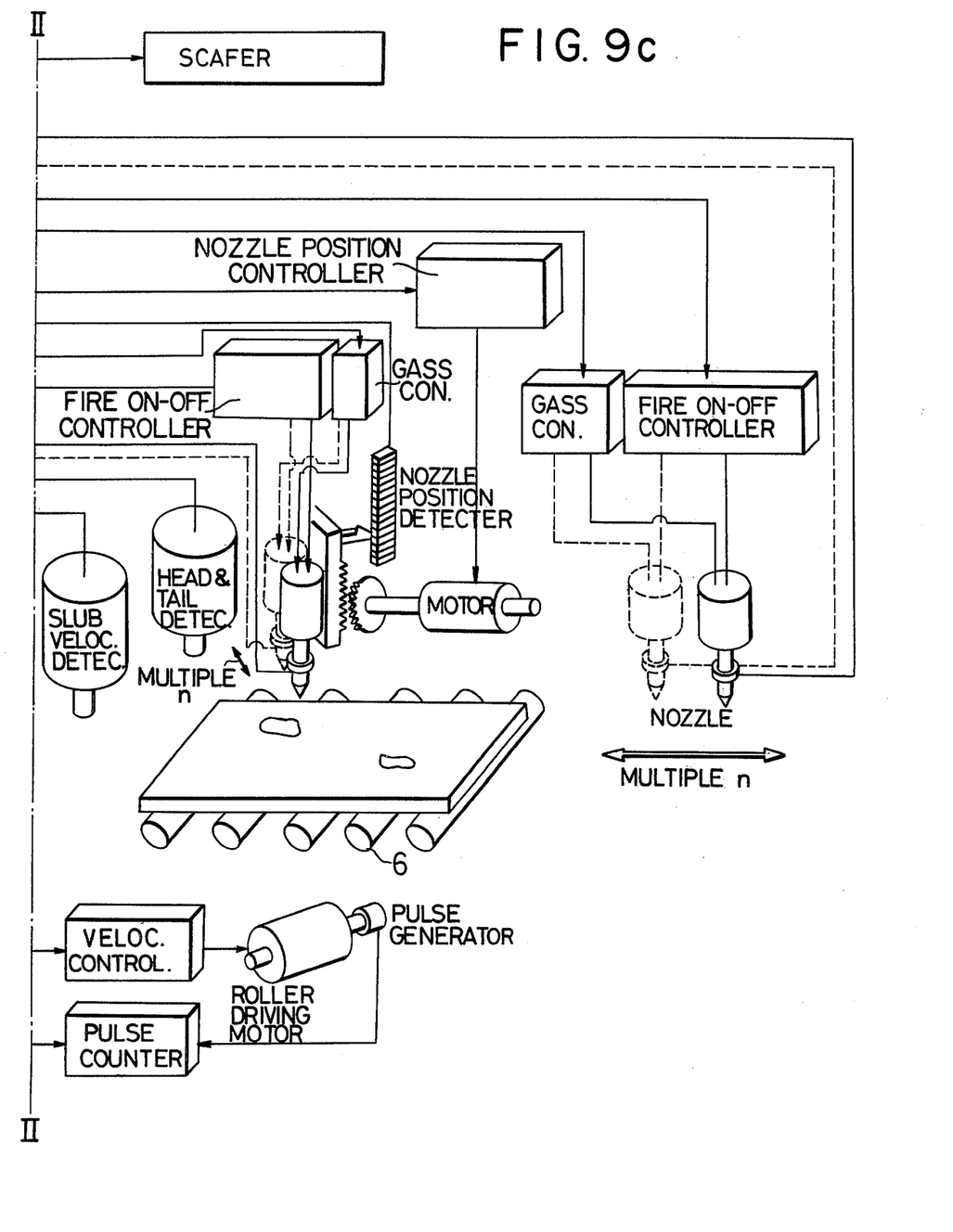

FIGS. 9a, 9b and 9c show parts of an automatic scarfing system, which form a complete view by coinciding the lines on the right-hand end of FIG. 9a with the corresponding lines at the left-hand end of FIG. 9b. In the same way, FIGS. 9b and 9c can be combined. The system has the same general arrangement as that shown in FIG. 6. A metal piece 10, which is a slab in the present example, is previously marked manually with patterns and is transferred on a table roller 1 for scanning by a mark detector 2p which is provided for sensing the marks on the upper surface of the slab. The detected patterns are input into the computer 3 through a control unit 11p which is associated with the upper surface. The slab width and thickness are also detected by the mark detector 2p and another mark detector 2s, respectively, the latter being associated with the lateral edge face. And these informations are also input into the computer 3 through the control unit 11p and another control unit 11s, respectively. In this manner, the mark detectors 2p and 2s examine the presence or absence of patterns indicating surface defects for the respective mesh portions which are divided along the width and the length of the slab beginning with the leading edge. As mentioned previously, the detectors 2s and 2p may be industrial television cameras of which scanning lines are assigned to length portions of the metal piece. In addition, the length portions of the metal piece is also switched for each frame thereby dividing the entire surface of the metal piece into a mesh configuration. In order to compensate for the error in the position of the mark signals which may result from a crosswise or a vertical movement of the slab on the roller table, the mark detectors 2s, 2p also feed collection signals into the computer through the respective control units 11s, 11p. The mark detectors 2s, 2p receive focus adjusting signals from the control computer 3.

The speed with which the individual rollers of the roller table 1 rotate is manually controlled by an operator, through a roller table drive motor 12. A pulse generator 13 is operatively connected with the motor 12 and converts the speed of the roller table into a train of pulses, which are counted by a pulse counter 14 for inputting an actual speed signal into the computer 3.

In response to the mark signals, the collection signals and the actual speed signals input, the computer 3 initially performs a pattern recognition by forming the metal surface image into a mesh configuration within an address memory, thus storing the position and extent of surface defects. The computer also determines the type and depth of surface defects in accordance with the detected patterns, and calculates an optimum scarfing depth for each defect. Based on the information obtained as a result of the pattern recognition, the computer then performs an edition by editing the information relating to the defect which is supplied as the metal surface image in the mesh configuration into scarfing areas and by calculating an optimum scarfing depth for each scarfing area. Where the scarfing machine is a single nozzle machine, a minimum time scarfing procedure is also calculated. As a result of these data processings, the computer produces ignition and deactuation signals for the scarfing nozzles associated with the upper surface and the lateral edge faces, a control signal for the nozzle block, a speed command signal for the roller table and a gas flow rate control signal, which are applied to the scarfing machine and the slab conveyor.

The scarfing operation which takes place by the action of the scarfing machine is fed back to the computer in the form of an ignition and a deactuation status signal of the scarfing nozzles, a position signal from the nozzle block, a leading and tail end detection signal, slab speed signal and an actual roller table speed signal. In response to these feedback signals, the computer controls the output signals fed to the scarfing machine so as to bring its operation to the established values. The head and tail end detection signal is input into the control computer 3 in order to control the start and the end of the operation of the scarfing machine and the computer in turn supplies a nozzle deactuation control signal to the scarfing machine.

While in the embodiment described above, the metal piece is manually marked with patterns, it will be understood that an automatic marking system can be combined with the system of the invention.

Having described the invention, what is claimed are:
1. A method of treating defects on or beneath the surface of a metal piece comprising the steps of:
   (a) marking directly on the surface of the metal piece with patterns formed by assigned colored marks of a specific size and shape which represent the position extent, type and depth of the defects;
   (b) optically detecting the colored marks with a mark detector;
   (c) storing the detected marks into an electronic computer as a metal surface image on a mesh configuration, the computer being able to recognize the position, extent, type and depth of the surface defects from the stored metal image;
   (d) electronically correcting for transverse shifts and editing the stored marks into unit scarfing areas;
   (e) electronically calculating an optimum scarfing depth for each scarfing area;
   (f) supplying the edited and calculated information to a scarfing machine to permit automatic scarfing of the surface detects.
2. A method of treating surface defects of a metal piece described in claim 1, wherein colors of marks represent depth of the surface defects of the metal piece.
3. A method of treating surface defects of a metal piece described in claim 1, wherein colors of marks represent type of surface defects of the metal piece.
4. A method of treating surface defects of a metal piece described in claim 1, wherein pattern of marks represent depth of surface defects of the metal piece.
5. A method of treating surface defects of a metal piece described in claim 1, wherein pattern of marks represent type of surface defects of the metal piece.
6. A method of treating surface defects of a metal piece described in claim 1, wherein the mark detector also detects head and tail edges of the metal piece.

7. A method of treating surface defects of a metal piece described in claim 6, wherein the mark detector also detects side edges of the metal piece.

8. A method as in claim 1 and further comprising the step of providing relative movement between the metal piece and the mark detector to permit detection of the marks.

9. A method as in claim 1 and further comprising the step of providing relative movement between the metal piece and the scarfing machine to permit scarfing of the surface defects.

* * * * *